United States Patent
Gibeault et al.

(10) Patent No.: US 6,324,891 B1
(45) Date of Patent: Dec. 4, 2001

(54) METHOD AND APPARATUS FOR MONITORING GAS(ES) IN A DIELECTRIC FLUID

(75) Inventors: Jean-Pierre Gibeault, Dollard-des-Ormeaux; Bernard Noirhomme, N.D. de l'Ile Perrot; Renyan Qin, St-Léonard, all of (CA)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/270,462

(22) Filed: Mar. 15, 1999

(30) Foreign Application Priority Data

Apr. 14, 1998 (CA) .................................................. 2235021

(51) Int. Cl.⁷ .......................... G01N 30/02; G01N 1/22; G01N 33/497; G01N 1/14
(52) U.S. Cl. ....................... 73/19.01; 73/19.12; 73/23.31; 73/863.83
(58) Field of Search ............................... 73/19.02, 19.12, 73/23.31, 25.01, 31.06, 863.83, 19.01; 702/24

(56) References Cited

U.S. PATENT DOCUMENTS

| | | | |
|---|---|---|---|
| 4,271,474 | * 6/1981 | Belanger et al. | 702/24 |
| 4,293,399 | * 10/1981 | Belanger et al. | 204/424 |
| 4,444,040 | * 4/1984 | Sakai et al. | 73/19.02 |
| 4,508,598 | * 4/1985 | Giner | 205/782.5 |
| 5,070,738 | * 12/1991 | Morgan | 73/863.83 |
| 5,271,263 | * 12/1993 | GIbeault | 73/19.12 |
| 5,749,942 | * 5/1998 | Mattis et al. | 95/46 |
| 5,773,709 | * 6/1998 | Gibeault et al. | 73/25.01 |
| 5,834,627 | * 11/1998 | Ricco et al. | 73/23.31 |
| 6,037,592 | * 3/2000 | Sunshine et al. | 250/343 |
| 6,041,643 | * 3/2000 | Stokes et al. | 73/31.06 |

\* cited by examiner

Primary Examiner—Hezron Williams
Assistant Examiner—Jay L. Politzer
(74) Attorney, Agent, or Firm—Nixon & Vandehye P.C.

(57) ABSTRACT

An apparatus for monitoring one or more gas components in a fluid wherein either a) a sample gas obtained from the fluid is enriched in at least one target gas which is to be subjected to analysis;

b) at least one target gas which is to be subjected to analysis is separated from a sample gas obtained from the fluid; or c) both.

12 Claims, 3 Drawing Sheets

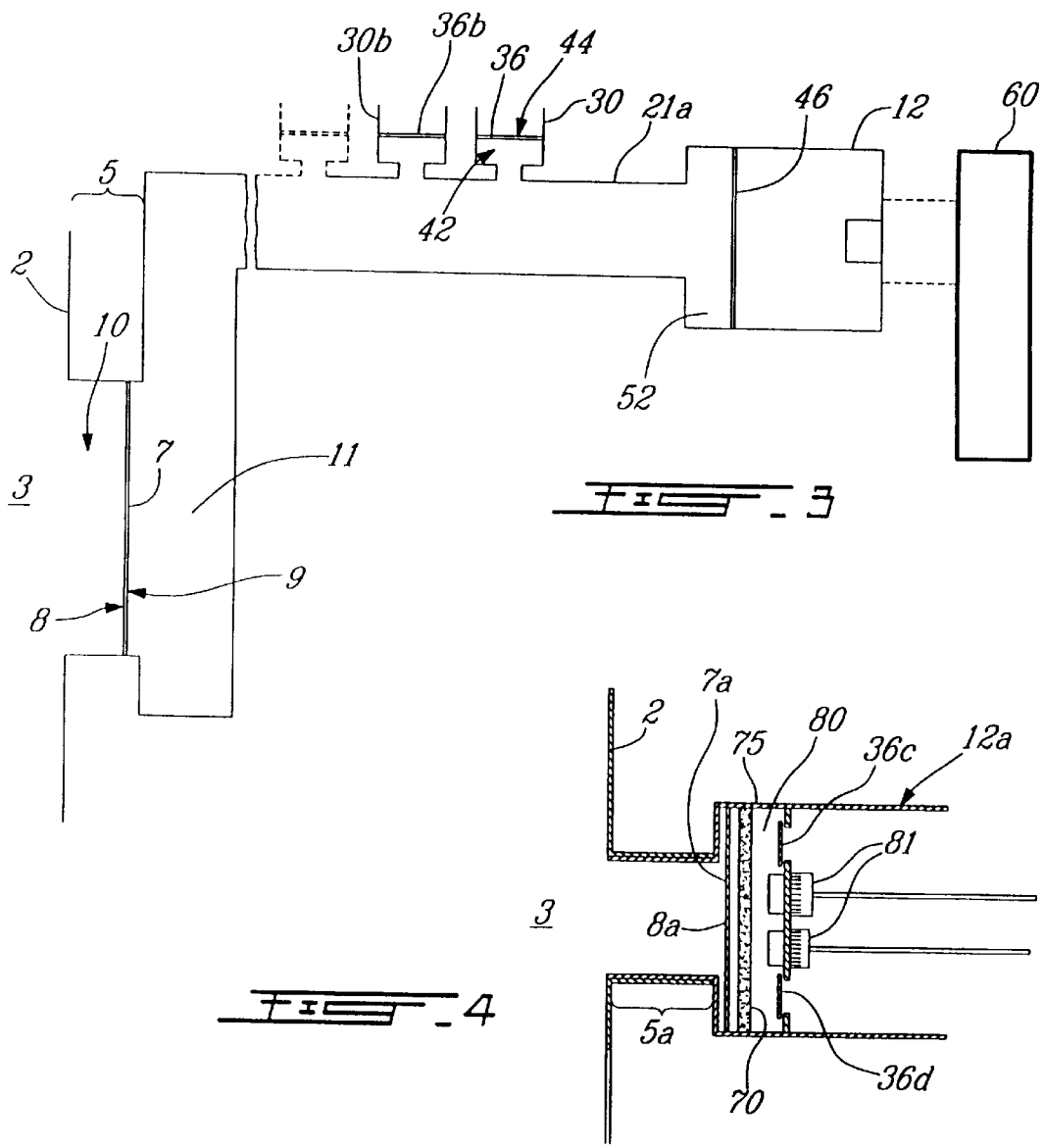
FIG. 3
FIG. 4
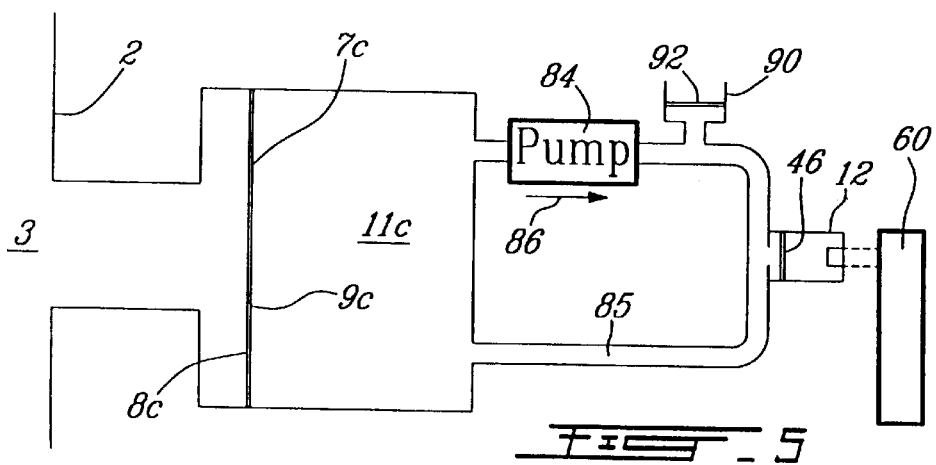
FIG. 5

METHOD AND APPARATUS FOR MONITORING GAS(ES) IN A DIELECTRIC FLUID

FIELD OF THE INVENTION

The present invention relates generally to a means and a method for monitoring the presence of one or more gases in a fluid such as, for example, a dielectric fluid. The present invention in particular relates to the monitoring of one or more gas components in a fluid wherein either a) a sample gas obtained from the fluid is enriched in at least one target gas which is to be subjected to analysis;

b) at least one target gas which is to be subjected to analysis is separated from a sample gas obtained from the fluid; or c) both.

The present invention may in particular, for example, be exploited as part of a means for the monitoring (e.g. detection of) one or more substances in fluid insulated electrical equipment, e.g. to monitor incipient failure conditions. The dielectric fluid may be a dielectric liquid (e.g. oil) or a dielectric gas. More particularly, the present invention relates to an apparatus and method far monitoring one or more gas components in a dielectric fluid disposed in an interior of an electrical system wherein a sample gas obtained from the dielectric fluid is enriched in at least one target gas which is to be subjected to analysis and/or at least one target gas which is to be subjected to analysis is separated from a sample gas obtained from the dielectric fluid.

BACKGROUND OF THE INVENTION

The following will deal, by way of example only, with the detection of a gas in a fluid which is a dielectric fluid.

Electrical systems are well known in the art which use a dielectric fluid as an insulating substance; these systems include for example transformers, circuit breakers and the like.

It is known that, in the event of a disturbance or malfunction of an above mentioned type of device or system, the result may be the production of one or more undesired gases in the insulating fluid; this may occur for example if a device is working at high temperature or high conditions of electrical stress therein. Such conditions may also produce undesired moisture and/or one or more breakdown products of the dielectric material of the insulating system (i.e. insulating fluid). If such abnormal conditions are allowed to continue uncorrected, this may lead to irreparable damage to the electrical system. A timely (e.g. more or less immediate) detection and/or diagnosis of any such abnormal operation of an electrical apparatus is thus advantageous in order to be able to avoid irreparable harm to such a system.

Accordingly, various monitoring devices and systems have been proposed for the detection of any incipient failure conditions such as for example any undesired increase of the concentration of a fault gas (e.g. a combustible gas such as for example, hydrogen gas, carbon monoxide gas, methane gas, ethane gas, ethylene gas, acetylene gas and the like or a non-combustible gas such as for example, carbon dioxide), moisture (e.g. water), a breakdown product, contaminant substance, and/or the like contained (e.g. dissolved) in the insulating fluid.

Some such detection and/or monitoring systems are, for example, described in Canadian Patent no. 1,054,223 (Bélanger), U.S. Pat. No. 4,112,737 (Morgan), U.S. Pat. No. 4,293,399 (Bélanger et al), U.S. Pat. No. 4,271,474 (Bélanger et al), U.S. Pat. No. 5,070,738 (Morgan) and U.S. Pat. No. 5,271,263 (Gibeault). The entire contents of these patent references as well as any other patent or other types of references which are mentioned therein are incorporated herein by reference.

For example, U.S. Pat. No. 4,293,399 describes how the concentration of gaseous hydrogen dissolved in a fluid may be determined by a measure of an electric current generated by electro-chemical oxidation of the gaseous hydrogen at an electrode of the detector. The prior art detecting and measuring means described in this U.S. patent comprises a polymeric membrane permeable to hydrogen gas for contact with a fluid containing dissolved hydrogen gas; an electrolyte capable of facilitating oxidation of the hydrogen gas diffused through the polymeric membrane at a first electrode and reduction of an oxygen-containing gas such as air at a second electrode; and a measuring device connected across the electrode for measuring the intensity of the electrical current generated by the electrochemical reaction of oxidation of the hydrogen gas, this intensity being proportional to the concentration of hydrogen in the fluid.

It is advantageous for such monitoring (e.g. detection) devices, as described above, to be able to provide an accurate as possible detection and/or diagnosis of the incorrect operation of systems such as, for example, transformers, circuit breakers, shunt reactors or any electro-apparatuses using a dielectric fluid as an insulating substance such as a dielectric liquid (e.g. a dielectric oil) or a dielectric gas (e.g. $SF_6$ gas).

A number of the above mentioned prior art monitoring devices or systems have the drawback that the sample gas received by the detector may have a relatively low concentration of a target gas which it is desired to detect or monitor; e.g. a low concentration of acetylene gas relative to hydrogen gas. In such case, the low concentration of a target gas relative to the other gases present in a sample gas may be such that one or more of the other gases may interfere with the measurement of a predetermined target gas(es). In other words, the precision of the results of the detecting or monitoring device may thus be less than is desired; i.e. due to that fact that one or more extraneous gases may interfere with the reading of the target gas.

Accordingly, it would be advantageous to be able to facilitate analysis (e.g. detection) of one or more predetermined individual gases (i.e. target gases) of a sample gas mixture. It would, in general, be advantageous to be able to obtain a sample gas enriched in a target gas, the presence of which is to be the subject of an analysis and/or separate from a sample gas mixture at least one target gas which is to be subjected to analysis. It would, further be advantageous to be able to facilitate analysis of target gases of a sample gas by separating one or more such target gases from the sample gas, the so separated target gas then being subjected to detection.

SUMMARY OF THE INVENTION

It is to be understood herein that the expression "detection component" as well as the words "detst", "detecting" and the like include, but are not limited to, activities which involve checking for a substance, detecting a substance, determining the presence of a substance, etc.

It is also to be understood herein that the expression "analysing means for monitoring" as well as the words "monitor", "monitoring" and the like include, but are not limited to, one or more activities which involve checking for a substance, detecting a substance, keeping track of a substance, determining the presence of a substance, the continuous measurement of a substance, the intermittent measurement of a substance, etc.

Accordingly, the present invention provides in an apparatus for detecting a gas in a fluid, the apparatus comprising:

a gas extraction component for extracting a sample gas mixture from said fluid, said sample gas mixture comprising a target gas, and a detection component for detecting the presence of said target gas, the improvement wherein said apparatus includes a gas removal component for preferentially removing a predetermined gas component of said sample gas mixture, said gas removal component comprising a gas-permeable element through which said predetermined gas component is able to preferentially pass.

In accordance with another aspect of the present invention there is provided in an apparatus for detecting a gas in a fluid, the apparatus comprising:

a wall component defining a gas chamber, a gas extraction component comprising a first gas-permeable element through which a gas mixture is able to pass from said fluid into said gas chamber, said wall component comprising said first gas-permeable element, said gas mixture comprising a target gas, a detection component for detecting the presence of said target gas the improvement wherein said apparatus includes a gas removal component for preferentially removing a predetermined gas component of said sample gas mixture, said gas removal component comprising a second gas-permeable element through which a predetermined gas component of said sample gas mixture is able to preferentially pass.

In accordance with the present invention the wall component may comprise said second gas-permeable element and the detection component may be configured for detecting the presence of the target gas in said gas chamber.

In accordance with a further aspect the present invention provides in an apparatus for monitoring one or more gases in a fluid, the apparatus comprising:

a gas extraction component for extracting a sample gas mixture from said fluid, said sample gas mixture comprising one or more target gases and an analysing component for monitoring the presence of said one or more target gases, the improvement wherein said apparatus includes a gas removal component for preferentially removing one or more predetermined gas components of said sample gas mixture, said gas removal component comprising one or more gas-permeable elements through which one or more respective predetermined gas components is able to preferentially pass.

In accordance with a particular aspect of the present invention, an above described apparatus may be an apparatus for detecting a gas in a dielectric fluid, said fluid being in an interior of an electrical system.

In accordance with an additional aspect the present invention provides in a method for detecting a gas in a fluid, the method comprising:

extracting a sample gas mixture from said fluid, said sample gas mixture comprising a target gas, and detecting the presence of said target gas, the improvement wherein said method includes preferentially removing a predetermined gas component of said sample gas mixture.

In accordance with the present invention the predetermined gas component may be preferentially removed from the sample gas mixture so as to obtain a detection sample gas having a proportion of the target gas(es) relative to said predetermined gas component which is (are) increased relative to the proportion thereof in the sample gas mixture and detecting the presence of the target gas(es) in said detection sample gas mixture.

In accordance with another particular aspect of the present invention, an above described method may be a method for detecting a gas in a dielectric fluid, said fluid being in an interior of an electrical system.

In accordance with the present invention the predetermined gas component may be the target gas component; in this case it is the separated gas which is to be detected, etc. . . .

As mentioned herein the predetermined gas component may comprise hydrogen gas while the target gas may be acetylene gas.

In accordance with the present invention a sample gas mixture mentioned in any of the above descriptions of the various aspects of the present invention may comprise two or more gases including one (or more) target gas(es).

The present invention in particular relates to an apparatus, (including a device, system and the like) which may be used to detect or more particularly to monitor one or more gaseous substances (i.e. target gas(es)) in a fluid which are indicative of incipient failure conditions in fluid insulated electrical equipment or systems; i.e. to detect and in particular to monitor the presence, concentration, etc, of such a substance over time. The apparatus may, for example, be used to detect the presence of gaseous substances contained in the insulating fluid of transformers such as for example fault gases, moisture or breakdown products (see above).

The present invention also relates to an apparatus wherein a dielectric fluid (e.g. liquid or gas) may be monitored (e.g. sampled and tested) by being withdrawn from and returned to the interior of an electrical system by any suitable known means.

The gaseous substance(s) to be detected and in particular to be monitored may, for example, comprise a member of the group comprising a fault gas (e.g. a combustion gas such as for example, hydrogen gas), moisture (e.g. water) and/or a breakdown product. The gas components which it may be sought to detect may, for example, be selected from the group of gases comprising hydrogen, carbon monoxide, carbon dioxide, moisture (i.e. $H_2O$), methane, ethane, ethylene and acetylene.

The fluid may be any dielectric fluid (e.g. liquid or gas) including the fluids mentioned above.

The gas extraction means and the gas removal means may each comprise a gas permeable element which may be of any desired (known) suitable and appropriate configuration, thickness, etc as well as of any (known) suitable and appropriate material which is permeable to the predetermined gas component or gas components which it may be desired to eliminate and/or detect; e.g. the gas permeable element may comprise a polymeric membrane, a metal membrane, etc. The gas permeable element may be flexible or rigid as desired or required.

If the gas components to be extracted from a dielectric fluid include hydrogen and acetylene, the gas permeable element of the gas extraction means may for example be a suitable membrane of a material such as silicone, fluorosilcone, polyethylene, polypropylene, etc.

The tables A and B below show the extraction efficiency of a polypropylene (PP) membrane (thickness: 0.18 mil) and a low density polyethylene (LDPE) membrane (thickness: 1 mil.). The polypropylene (PP) membrane and the low density polyethylene (LDPE) membrance were both obtained from Goodfellow Corporation, Berwyn, Pa., U.S.A. The extraction efficiency has been measured for some fault gases detected in transformer oil. The results are expressed in % of equilibrium value versus time to fill a cavity of 10 mL; for the tables A and B the gas extracted through the respective membranes was collected for quantification or measurement in a Fourier Transform Infra-Red measurement cell.

TABLE A (0.004 mm PP), 55° C.

| Ext. Time | $CH_4$ | $C_2H_6$ | CO | $C_2H_4$ | $C_2H_2$ | $CO_2$ | RH % |
|---|---|---|---|---|---|---|---|
| 1 hr | 26% | 0% | 12% | 27% | 39% | 50% | 79% |
| 3 hrs | 50% | 4% | 28% | 58% | 67% | 80% | 86% |
| 5 hrs | 67% | 30% | 43% | 78% | 89% | 100% | 93% |
| 10 hrs | 89% | 77% | 75% | 100% | 100% | — | 100% |

TABLE B (LDPE), 55° C.

| Ext. Time | $CH_4$ | $C_2H_6$ | CO | $C_2H_4$ | $C_2H_2$ | $CO_2$ | RH % |
|---|---|---|---|---|---|---|---|
| 1 hr | 20% | 6% | 16% | 44% | 42% | 64% | 78% |
| 3 hrs | 45% | 58% | 39% | 79% | 75% | 91% | 89% |
| 5 hrs | 62% | 82% | 55% | 91% | 89% | 100% | 100% |
| 10 hrs | 88% | 100% | 80% | 100% | 100% | | |

If the gas component to be eliminated from an extracted gas sample is hydrogen, the gas permeable element of the gas elimination means may for example be a suitable membrane of a material such as teflon, palladium, a hydrogen porous ceramic, etc.

In accordance with the present invention a polyethylene membrane (obtained for example from Goodfellow Corporation) may be used for the initial gas extraction stage while a teflon membrane (obtained for example from Goodfellow Corporation) or Palladium on frit disc (obtained from Palladium evaporation with an electron beam instrument (E-Beam)) may be used for the subsequent gas elimination stage (e.g. for the elimination or separation of hydrogen gas).

The table C below show typical combination of extraction and elimination membrane as well as their elimination efficiency.

TABLE C

Elimination of hydrogen have been achieved with the following membrane combination:

| Extraction membranes | Elimination membrane | Efficiency |
|---|---|---|
| Polyethylene | Teflon (.25 mil) | 95% |
| Polyethylene | Palladium on frit disc | 99% |

Hydrogen gas may, for example be present in a sample gas at 1000 ppm while a target gas such as acetylene may only be present at 5 ppm. In this case he hydrogen gas may interfere with the detection of acetylene. In accordance with the present invention in order to facilitate the detection of acetylene, the hydrogen gas may be eliminated from the sample gas such that the hydrogen gas may be present at 50 ppm and acetylene at 5 ppm.

In accordance with the present invention, it is to be understood that the attachment of an apparatus for detecting or monitoring a substance may be a direct attachment or an indirect attachment. In the case of a direct attachment, the apparatus may, for example, be connected directly to an access opening by a wall component defining a fluid pocket component without any intervening tube or pipe like members; please see FIG. 2 of U.S. Pat. No. 4,293,399 for an example of a direct attachment to a system. In the case of an indirect attachment, the apparatus may, for example, be connected to a system via a valve; such connection will permit the easy removal of the apparatus from a system without, for example, the necessity of emptying the system or at least reducing the level of fluid in order to avoid spillage of fluid if for example the monitoring apparatus must be replaced or repaired. The valve in this later case, will define a part of the fluid pocket. Please see U.S. Pat. No. 5,271,263.

The detector and/or analysing means may take on any desired or necessary form. In accordance with the present invention, a detector may take on the configuration of the detector device described in U.S. Pat. No. 4,293,399. The analysing means may, for example, comprise an electrochemical detector, a semi-conductor detector, a metal oxide detector, a capacitive detector (e.g. for water), a chromatograph (e.g. a gas chromatograph), an IR detector, a spectrograph (e.g. I.R. spectrophotometer) and the like.

An analysing means may, for example, comprise an extraction or isolation member for isolating a gaseous substance from a dielectric liquid or gas, the member being disposed for contacting dielectric liquid or gas. The extraction or isolation member may, for example, as mentioned above comprise a membrane, permeable to a gaseous substance and impermeable to said dielectric liquid or gas, the membrane being disposed for contacting, on one side thereof, dielectric liquid or gas; see for example the above referred to U.S. Pat. No. 4,293,399.

The following will deal in particular with dielectric liquids and transformer type electrical systems. However, it is to be understood that this is done by way of example only. The invention is applicable to other types of fluids and electrical systems.

In the drawings which illustrate example embodiments of the invention:

FIG. 3 is a schematic illustration of a further example gas monitoring apparatus in accordance with the present invention wherein means are provided for the elimination of a plurality of extraneous gases from a gas sample;

FIG. 4 is a schematic illustration of an example gas detector apparatus in accordance with the present invention;

FIG. 5 is a schematic representation of a further example gas monitoring apparatus in accordance with the present invention;

FIG. 7b is a schematic end view representations of the extractor part shown in FIG. 7a;

FIG. 8b is a schematic end view representations of the gas removal or eliminator part shown in FIG. 8a.

Figure 1:
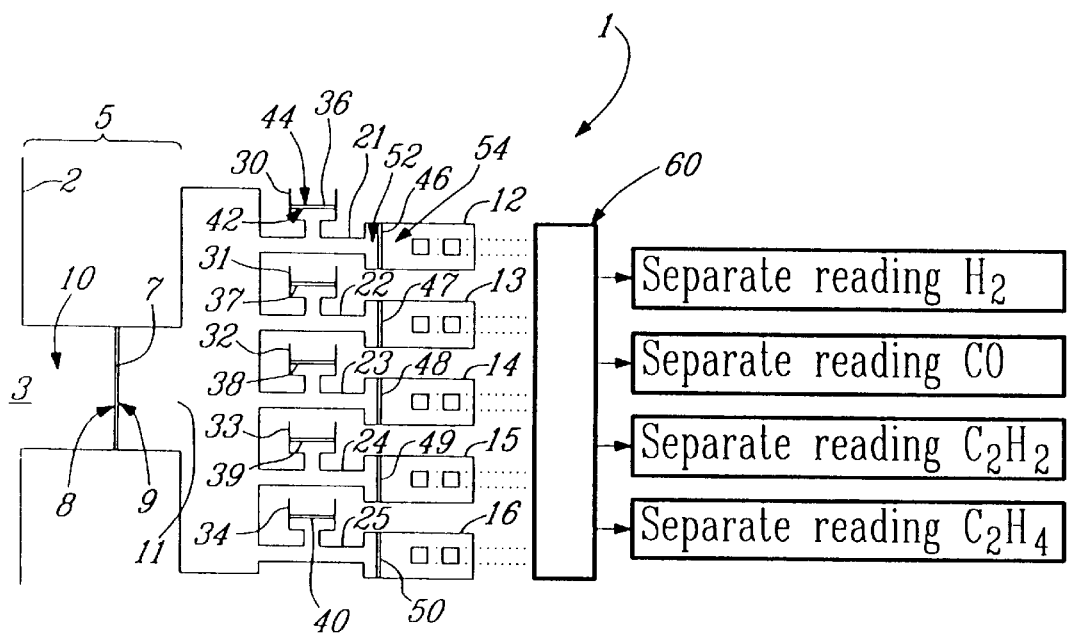
FIG. 1 is a schematic illustration of an example gas monitoring apparatus in accordance with the present invention wherein a gas elimination means is disposed after a gas extraction means.

Referring to FIG. 1, a gas monitoring apparatus in accordance with the present invention, generally designated by the reference numeral 1, is shown as being more or less direct connected to the housing wall 2 of an electric transformer system (e.g. there is no intervening valve member); only a portion of the wall 2 is shown along with a portion of a dielectric liquid 3. The dielectric liquid 3 is disposed within the transformer housing.

The gas monitoring apparatus includes a tubular member 5. The tubular member 5 may for example be connected to a fluid access opening of the transformer system; please see U.S. Pat. No. 4,112,737.

The interior of the tubular member 5 is blocked off by a gas permeable extraction membrane 7 such that the tubular member 5 is divided into two parts and the extraction membrane 7 has a transformer side 8 and a gas cavity side 9. As may be seen one part of the tubular member 5 is in fluid communication with the interior of the transformer housing such the dielectric liquid 3 in the housing may contact the transformer side 8 of the gas permeable extraction membrane 7 in a fluid pocket 10. The other part of the tubular member 5 is in fluid communication with the interior of a gas extraction cavity or chamber 11 for receiving a sample gas. The gas permeable extraction membrane 7 is of any suitable material capable of allowing predetermined gases in the dielectric liquid 3 to diffuse therethrough into the chamber 11 (e.g. hydrogen, acetylene, etc.).

A number of gas analysis detectors 12, 13, 14, 15 and 16 are each connected to the gas chamber wall 18 by respective fluid communication members 21, 22, 23, 24 and 25 whereby the detectors 12, 13, 14, 15 and 16 are in gas communication with the gas cavity 11.

A gas elimination means 30, 31, 32, 33 and 34 is connected to each of the gas communication members 21, 22, 23, 24 and 25. The gas elimination means 30, 31, 32, 33 and 34 each comprise an gas elimination or removal membrane 36, 37, 38, 39 and 40 having a respective extraction cavity side and a respective elimination chamber side. Referring to the gas elimination means 30 by way of example the extraction cavity side is designated by the reference numeral 42 and the elimination chamber side is designated by the reference numeral 44. The elimination chamber sides each defines a portion of the wall of an elimination chamber (only a portion of which is shown) from which the eliminated gas passing through the elimination membranes may be exhausted to the atmosphere, be sent on to an additional gas detector means, or be otherwise disposed of. The gas elimination membranes 36, 37, 38, 39 and 40 are each of any suitable material capable of allowing predetermined extraneous gas(es) in the sample gas to diffuse therethrough into the respective elimination chamber (e.g. hydrogen).

In the example apparatus shown the analysis detectors 12, 13, 14, 15 and 16 have a detector housing in which is disposed the various elements thereof. The analysis detectors 12, 13, 14, 15 and 16 in particular each have a detector membrane 46, 47, 48, 49 and 50 which divides respective detector housings into an extraction cavity side and a detector side; the detector side being provided with, suitable gas detection means. Referring to the analysis detector 12 by way of example the extraction cavity side is designated by the reference numeral 52 and the detector side is designated by the reference numeral 54. The analysis detectors may for example take on the general structure of the detector shown in U.S. Pat. No. 4,112,737. The detector membranes are each of any suitable material capable of allowing predetermined target gases in respective detection gas samples on the extraction cavity side thereof to diffuse therethrough into the detector side (e.g. hydrogen, acetylene, etc.).

The analysis detectors 12, 13, 14, 15 and 16 are each in turn electronically coupled in any known fashion (illustrated by dotted lines) to an appropriate electronic reading system (s) designated generally by the reference numeral 60 which is able to interpret the signals provided from the detectors so as to provide gas component readings and which may also include digital display elements for providing a visual reading with respect to the presence of a particular gas component.

An gas extraction membrane is as mentioned above of a material which is able to allow gases in the dielectric fluid to pass therethrough into a gas extraction cavity or chamber.

An gas elimination or removal membrane is as mentioned above of a material which is able to allow a predetermined extraneous gas in the gas sample in the extraction cavity to pass therethrough into the elimination chamber.

A detector membrane is as mentioned above of a material which is able to allow a predetermined target gas in the detection gas sample to pass therethrough into the detection chamber for interaction in known manner with any suitable gas detection mechanism; the detector membrane may of course be such that other gas(es) in addition to the target gas may also pass therethrough.

Figure 2:
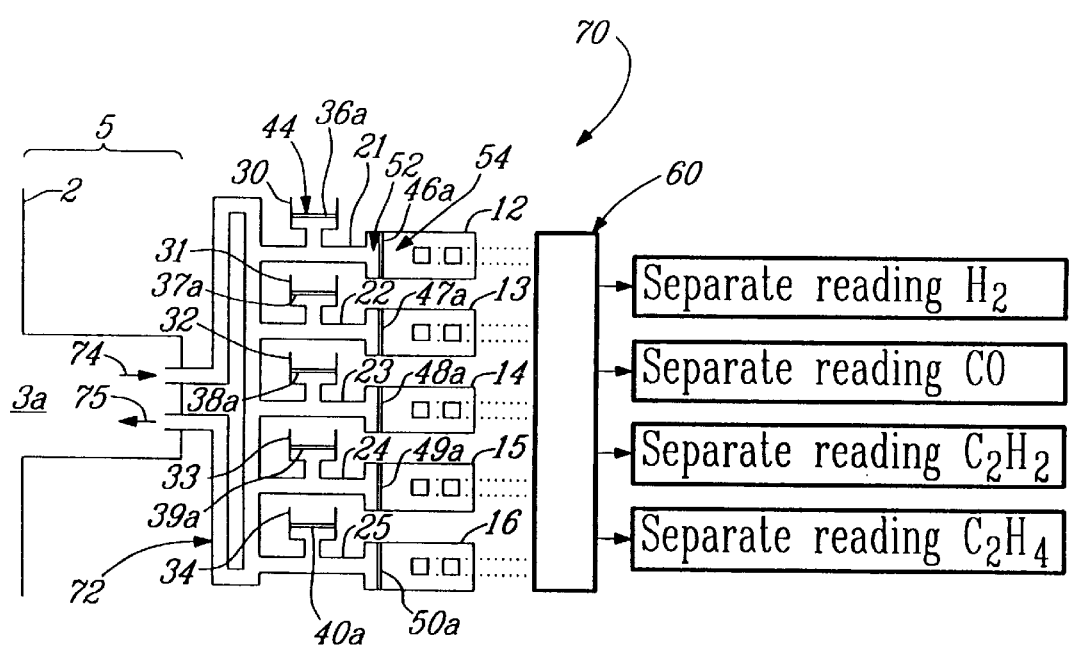
FIG. 2 is a schematic illustration of another example gas monitoring apparatus in accordance with the present invention wherein a gas elimination means is disposed before a gas extraction means.
Figure 6:
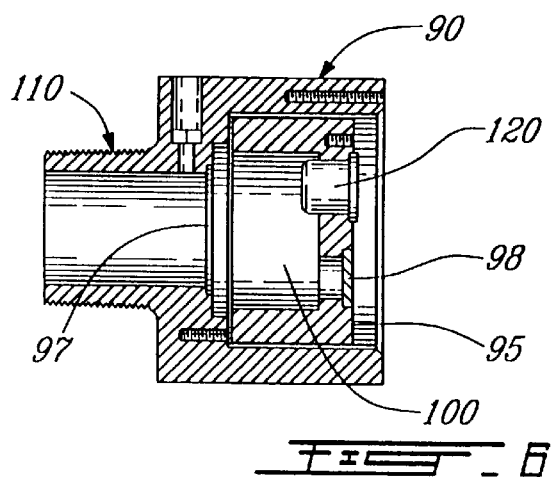
FIG. 6 is a schematic cross sectional view of a two part housing for another example gas detector apparatus in accordance with the present invention.

Referring to FIG. 2, this figure illustrates a modified version of the gas monitoring apparatus as shown in FIG. 1 generally designated by the reference numeral 70; the same reference numerals are used to designate common elements. The apparatus 70 shown in FIG. 2 may be used when the dielectric fluid is a dielectric gas and differs from the apparatus 1 shown in FIG. 1 in that there is no extraction membrane before the gas elimination means for initially separating gas from the dielectric gas. Instead the apparatus 70 includes a dielectric fluid circulation loop or circuit 72 in which dielectric fluid 3a is pumped (by a pumping mechanism not shown) from the interior of the transformer housing past the fluid communication members 21, 22, 23, 24 and 25 and back into the transformer housing in the direction of the arrows 74 and 75; please see U.S. Pat. No. 5,271,463 which illustrates an example of a fluid circulation loop.

As may be appreciated from the above, the elimination membranes 36a, 37a, 38a, 39a and 40a are each of a respective material which is able to allow a predetermined extraneous gas in the dielectric gas to pass therethrough into the elimination chamber. Similarly, the detector membranes 46a, 47a, 48a, 49a and 50a are also each of a respective material which is able to allow a detection gas sample comprising a predetermined target gas to pass from the dielectric gas therethrough into the detection side of the respective analysis detectors.

The apparatus shown in FIG. 3 is similar to the apparatus shown in FIG. 1 in that it has an extraction membrane 7 and a gas cavity 11. However the apparatus is provided with a single analysis detector 12 and a plurality of gas elimination means (two of which are designated with the reference numerals 30 and 30b) connected to a common gas communication member 21a; an additional gas elimination means is shown in dotted out line only. The gas elimination means 30 and 30b each comprise a respective elimination membrane 36 and 36b permeable to a different gas for reducing the content of a plurality of extraneous gases in the detection sample gas such that the proportion of a desired target gas or gases is raised with respect to each of the types of eliminated gas or gases.

FIG. 4 illustrates in schematic fashion an example gas detector apparatus 12a in accordance with the present invention. The detector is direct connected to the housing wall 2 of the above mentioned electric transformer system (i.e. with respect to FIG. 1). The detector 12a comprises an gas permeable extraction membrane 7a, a gas porous disk 70 (for maintaining the mechanical rigidity of the membrane 7a)and two gas elimination or removal membranes 36c and 36d; these elements are disposed in a detector housing having a wall component (designated generally by the reference numeral 75) defining gas cavity or chamber 80. The gas elimination or removal membranes 36c and 36d may for example be of a material which provides for the elimination of hydrogen gas from the detection gas sample in the detection gas cavity 80. As may be seen the wall component 75 includes the gas permeable extraction membrane 7a as well as the two gas elimination or removal membranes 36c and 36d. The detector 12a includes a target gas sensor array 81 which may be connected to a suitable measuring device (not shown). As may be appreciated the extraction membrane 7a incorporates the function of a detector membrane shown in FIGS. 1 to 3. This detector configuration may, for example, be used to eliminate hydrogen gas, as the interfering gas, in order to measure acetylene as the target gas.

FIG. 5 shows an alternate configuration for a gas monitoring apparatus which is direct connected to the housing wall 2, i.e. see FIG. 1. The gas monitoring apparatus is similar to that shown FIG. 3. For example, the apparatus has an extraction membrane 7c having a transformer side 8c and a cavity side 9c However, the apparatus has only a single gas extraction means 12 and is provided with a suitable gas pump 84 and a gas loop circuit 85 about which the sample gas is circulated in the direction of the arrow 86 from the gas cavity 11c past the gas extraction means 90 and single analysis detector 12 back to the gas cavity 11c. The extraction means 90 has an elimination membrane 92. The use of a pump allows for the exploitation of a relatively large extraction cavity 11c.

FIGS. 6, 7a, 7, 8a and 8b illustrate in schematic fashion a two part housing for another example gas detector apparatus in accordance with the present invention. The housing has a gas extractor part 90 and a gas removal or eliminator part 95. The gas extractor part 90 has a gas permeable extraction membrane 97. The gas removal or eliminator part 95 has a gas permeable elimination or removal membrane 98. The membranes 97 and 98 may beheld in place in any suitable manner, e.g. by an adhesive. As may be seen from FIG. 6 the eliminator part 95 is sized to slidingly fit within the extractor part 90 so as to be able to define a gas chamber 100.

Figure 7A:
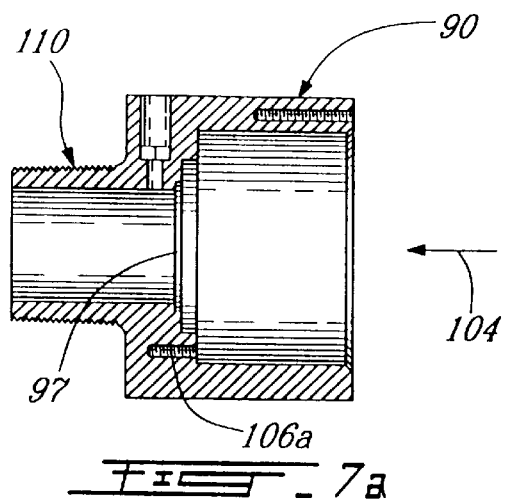
FIG. 7a is a schematic cross sectional representation of a gas extractor part of the two part housing shown in FIG. 6.
Figure 7B:
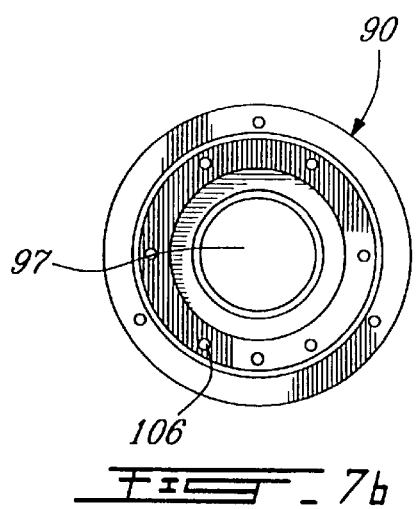
Figure 8A:
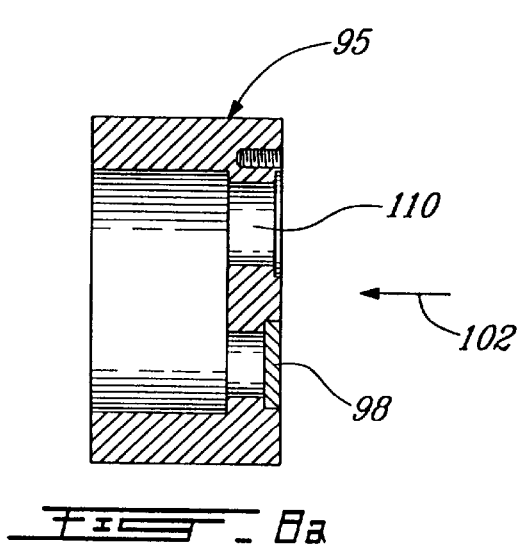
FIG. 8a, is a schematic cross sectional representation of a gas removal or eliminator part gas removal or eliminator part of the two part housing shown in FIG. 6.
Figure 8B:
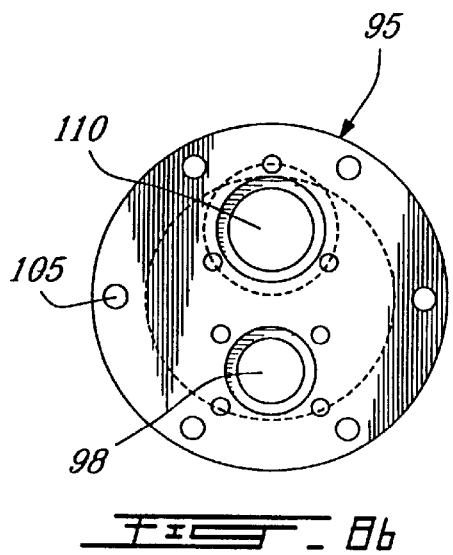

The eliminator part 95 may be maintained in place in the extractor part by six screw threaded bolts (not shown). FIG. 7b is a view of eliminator part 95 in the direction of the arrow 102 whereas the FIG. 8b is a view of the extraction part 90 in the direction of the arrow 104. Referring to FIG. 7b the eliminator part 95 is provided with six bolt openings sized to receive the stem of the above mentioned screw bolts; one of the openings is designated by the reference numeral 105. The extraction part 90 is provided with six corresponding screw threaded bolt openings one of which is designated in FIG. 8b by the reference numeral 106 (and in FIG. 8a by the reference numeral 106a). The bolt openings of each of the housing parts are so disposed that they may be aligned with one another so that a screw bolt may pass through a bolt opening of the elimination part and be screw engaged into a corresponding bolt opening of the extractor part for clamping the two parts together.

Although not shown, a suitable annular or ring gasket may be provided between the two housing parts for facilitating gas tight engagement between the two housing parts; the gasket being provided with six openings alignable with the bolt openings the two housing parts.

Referring back to FIG. 6 the extractor part is provided with a tapered outer screw threaded projection 110; the projection 110 maybe used to couple (i.e. screw) the detector housing to an inner threaded access opening of an electrical system. As shown in FIGS. 7a and 7b the elimination part is provided with an opening 115 for recieving a suitable gas sensor; in FIG. 6 a gas sensor 120 is show as being engaged (e.g. press fit) in the opening 115.

The embodiments of the invention in which an exclusive property or privilege is claimed are as defined as follows:

What is claimed is:

1. A system for detecting at least one target gas from a sample gas of a dielectric fluid of an electrical system, the system for detecting comprising:

at least one gas extraction cavity that receives the dielectric fluid, the dielectric fluid may comprise the sample gas and target gas;

at least one gas analysis detector that generates a signal if the at least one gas analysis detector is in contact with the target gas;

at least one fluid communication member that connects the at least one gas extraction cavity to the at least one gas analysis detector to communicate the sample gas from the gas extraction cavity to the gas analysis detector;

at least one gas elimination means connected to the at least one fluid communication member for permitting extraneous gases other than the target gas to diffuse therethrough to an elimination chamber;

a reading system for interpreting signals from the at least one gas analysis detector that can detect the target gas;

wherein each gas analysis detector comprises:

a detector housing;

a detector membrane disposed in the detector housing dividing the detector housing into an extraction housing side and a detection housing side, the detection housing side being in communication with the at least one gas analysis detector, the detector membrane permitting the target gas to pass therethrough, whereby:

a target gas that is present in sample gas of a dielectric fluid from of an electrical system can pass from the at least one extraction cavity through the at least one fluid communication member to the at least one gas analysis detector that generates signals representative of the target gas for interpretation by the reading system.

2. The system according to claim 1, wherein the at least one gas extraction cavity comprises a gas-permeable membrane, the gas-permeable membrane allowing the sample gas to be separated from the dielectric fluid of the electrical system.

3. The system according to claim 1, wherein the number of gas analysis detectors is the same as the number of fluid communication members.

4. The system according to claim 1, wherein a plurality of gas extraction cavities is provided on one fluid communication member.

5. The system according to claim 1, wherein each fluid communication member comprises one gas extraction cavity.

6. The system according to claim 1, wherein the target gas comprises a hydrogen-containing gas.

7. The system according to claim 6, wherein the hydrogen-containing gas comprises acetylene.

8. The system according to claim 1, further comprising means for circulating the dielectric fluid in the system for detecting at least one target gas from a sample gas of a dielectric fluid of an electrical system.

9. The system according to claim 8, wherein the means for circulating the dielectric fluid in the system for detecting at least one target gas from a sample gas of a dielectric fluid of an electrical system comprises a pump.

10. A system for detecting at least one target gas from a sample gas of a dielectric fluid of an electrical system, the system for detecting comprising:

at least one gas extraction cavity that receives the dielectric fluid, the dielectric fluid may comprise the sample gas and target gas;

at least one gas analysis detector that generates a signal if the at least one gas analysis detector is in contact with the target gas;

at least one fluid communication member that connects the at least one gas extraction cavity to the at least one gas analysis detector to communicate the sample gas from the gas extraction cavity to the gas analysis detector;

at least one gas elimination means connected to the at least one fluid communication member for permitting extraneous gases other than the target gas to diffuse therethrough to an elimination chamber;

a reading system for interpreting signals from the at least one gas analysis detector that can detect the target gas;

wherein each gas analysis detector comprises:

a detector housing;

a detector membrane disposed in the detector housing dividing the detector housing into an extraction housing side and a detection housing side, the detection housing side being in communication with the at least one gas analysis detector, the detector membrane permitting the target gas to pass therethrough, whereby:

a target gas that is present in sample gas of a dielectric fluid from of an electrical system can pass from the at least one extraction cavity through the at least one fluid communication member to the at least one gas analysis detector that generates signals representative of the target gas for interpretation by the reading system; and wherein the at least one gas extraction cavity comprises a gas-permeable membrane, the gas-permeable membrane allowing the sample gas to be separated from the dielectric fluid of the electrical system.

11. A method for detecting at least one target gas from a sample gas of a dielectric fluid of an electrical system using the system of claim 1.

12. A method for detecting at least one target gas from a sample gas of a dielectric fluid of an electrical system using the system of claim 10.

* * * * *